US011685944B2

(12) United States Patent
Bjork et al.

(10) Patent No.: US 11,685,944 B2
(45) Date of Patent: Jun. 27, 2023

(54) SYSTEM AND METHOD FOR LIQUID CULTURE OF ANAEROBIC OR MICROAEROPHILIC MICROORGANISMS

(71) Applicant: NEOGEN FOOD SAFETY US HOLDCO CORPORATION, Lansing, MI (US)

(72) Inventors: Jason W. Bjork, Cottage Grove, MN (US); Adam J. Stanenas, Cottage Grove, MN (US); Wensheng Xia, Woodbury, MN (US)

(73) Assignee: NEOGEN FOOD SAFETY US HOLDCO CORPORATION, Lansing, MI (US)

( * ) Notice: Subject to any disclaimer, the term of this patent is extended or adjusted under 35 U.S.C. 154(b) by 258 days.

(21) Appl. No.: 15/308,622

(22) PCT Filed: May 13, 2015

(86) PCT No.: PCT/US2015/030491
§ 371 (c)(1),
(2) Date: Nov. 3, 2016

(87) PCT Pub. No.: WO2015/175611
PCT Pub. Date: Nov. 19, 2015

(65) Prior Publication Data
US 2017/0191108 A1      Jul. 6, 2017

Related U.S. Application Data

(60) Provisional application No. 61/994,153, filed on May 16, 2014.

(51) Int. Cl.
*C12Q 1/04* (2006.01)
*C12Q 1/26* (2006.01)
*C12N 1/20* (2006.01)

(52) U.S. Cl.
CPC .................. *C12Q 1/04* (2013.01); *C12N 1/20* (2013.01); *C12Q 1/26* (2013.01)

(58) Field of Classification Search
CPC .................................... C12M 1/14; C12Q 1/04
See application file for complete search history.

(56) References Cited

U.S. PATENT DOCUMENTS

| | | | | |
|---|---|---|---|---|
| 4,775,626 | A * | 10/1988 | Armenta | C12M 23/08 435/189 |
| 5,654,164 | A | 8/1997 | Gardiol et al. | |
| 5,955,344 | A | 9/1999 | Copeland et al. | |
| 2005/0205840 | A1 | 9/2005 | Farneth et al. | |
| 2009/0023612 | A1 | 1/2009 | Pfeiffer et al. | |
| 2009/0226651 | A1 | 9/2009 | Chisholm et al. | |
| 2009/0280522 | A1 | 11/2009 | Wilson | |
| 2012/0058919 | A1 * | 3/2012 | Wilson | A61K 31/407 506/10 |

FOREIGN PATENT DOCUMENTS

| | | |
|---|---|---|
| EP | 0 246 912 | 11/1987 |
| WO | 2008/013831 | 1/2008 |
| WO | 2014/025514 | 2/2014 |
| WO | 2015/061213 | 4/2015 |

OTHER PUBLICATIONS

Abeam ("Ascrobic Acid Assay Kit", 2012, available at www.abcam.com/ps/products/65/ab65656/documents/ab65656%20Ascorbic%20Acid%20Assay%20Kit%20Biological%20Samples%20(Website).pdf). (Year: 2012).*
By Kappeli ("A Convenient Method for the Determination of Oxygen Solubility in Different Solutions", 1981, Biotechnology and Bioengineering vol. XXIII 1897-1901) (Year: 1981).*
Vendruscolo ("Determination of Oxygen Solubility in Liquid Media", ISRN Chemical Engineering, 2012). (Year: 2012).*
Grammel ("Microaerophilic Cooperation of Reductive and Oxidative Pathways Allows Maximal Photosynthetic Membrane Biosynthesis in Rhodospirillum rubrum" Applied and Environmental Microbiology, 2003, vol. 69 Issue 11, 6577-6586) (Year: 2003).*
Product Brochure entitled "Oxyrase® for Broth—Product Insert" from Oxyrase, Inc. 2009 2 pgs.
Ludwig, R.A.; "Microaerophilic bacteria transducer energy via oxidative metabolic gearing"; Research in Microbiology; vol. 155; 2004; pp. 61-70.
Tran, T.T.; "Evaluation of Oxyrase® enrichment method for isolation of *Campylobacter jejuni* from inoculated foods"; Letters in Applied Microbiology; vol. 21; 1995; pp. 345-347.
Clark et al., "Oxygen requirements of strains of *Pseudomonas* and *Achromobacter*," 1972, *Canadian Journal of Microbiology*, 18(3):321-26.
Jacxsens et al., "Effect of high oxygen modified atmosphere packaging on microbial growth and sensorial qualities of fresh-cut produce," Dec. 30, 2001, *International Journal of Food Microbiology*, 71(2-3):197-210.
"Oxygen—Periodic Table," Royal Society of Chemistry [online], [updated on the internet in 2020], [retrieved from the internet on Jan. 15, 2020], <https://www.rsc.org/periodic-table/element/8/oxygen>, 2 pages.

(Continued)

*Primary Examiner* — Robert J Yamasaki
*Assistant Examiner* — Charles Zoltan Constantine
(74) *Attorney, Agent, or Firm* — Hylton-Rodic Law PLLC

(57) ABSTRACT

A culture system for culturing a microaerophilic or an anaerobic microorganism is provided. The culture system can include effective amounts of i) an enzyme of an oxidoreductase family and ii) a substrate for said enzyme, a container, and a predetermined volume of aqueous medium that supports growth of said anaerobic or microaerophilic microorganism. The enzyme can be selected from a group consisting of ascorbic acid oxidase and laccase. The effective amounts are effective to deplete dissolved oxygen in the predetermined volume to a concentration that facilitates growth of a microaerophilic microorganism or an obligately-anaerobic microorganism. A method of using the system is also provided.

17 Claims, No Drawings

(56) References Cited

OTHER PUBLICATIONS

"What is heavier: oxygen or carbon dioxide? Question Date: Mar. 17, 1998," UCSB Science Line—Materials Research Laboratory National Science Foundation [online], The Regents of the University of California [updated on the internet in 2017], [retrieved from the internet on Jan. 15, 2020], <http://scienceline.ucsb.edu/getkey.php?key=2966>, 3 pages.

* cited by examiner

SYSTEM AND METHOD FOR LIQUID CULTURE OF ANAEROBIC OR MICROAEROPHILIC MICROORGANISMS

CROSS REFERENCE TO RELATED APPLICATIONS

This application is a national stage filing under 35 U.S.C. 371 of PCT/US2015/030491, filed May 13, 2015, which claims priority to U.S. Provisional Patent Application No. 61/994,153, filed May 16, 2014, the disclosure of which is incorporated by reference in its entirety herein.

TECHNICAL FIELD

The present invention pertains to the selective culture and/or detection of anaerobic and/or microaerophilic microorganisms in a sample and particularly concerns a method of enriching a population of target anaerobic and/or microaerophilic microorganism(s) in a sample employing an enzyme-substrate system. There is also disclosed a means to facilitate the same.

BACKGROUND

Microorganisms are generally classified into different groups based on their need for, and tolerance of oxygen. "Aerobes" are microorganisms that require oxygen to grow. "Facultative aerobes" are microorganisms that are able to grow with or without oxygen. Another group of microorganisms include "microaerophiles" that can grow only in the presence of very low levels of oxygen. Finally, there a class of microorganisms called "anaerobes" that cannot tolerate oxygen as they may be either inhibited or killed by it. Oxygen sensitive bacteria must be cultivated under a controlled atmosphere and this necessitates the development of methods for their cultivation that are specifically directed towards total or limited exclusion of oxygen.

Enrichment culture is one of commonly employed methodology to culture and screen for the presence of target microorganisms in a sample. The conventionally known anaerobic culture methods being poorly suited for routine use where rapid and easy processing of numerous and varied samples is necessitated, there is need for an improved method for achieving anaerobiosis in a simple, rapid and highly efficient way. The food processing industries, which routinely test food and beverage samples for the presence of anaerobic or microaerophilic microorganisms, would clearly benefit by determining microbial contamination through such a quick, simple and convenient culture method. Other industries would also welcome the opportunity to detect contamination by anaerobic bacteria in a more rapid and effective way.

SUMMARY

While trying to solve many of the problems described here associated with culturing anaerobic and microaerophilic microorganisms, attempts have been made to devise an improved method to cultivate and/or screen for the presence of anaerobes and/or microaerophiles in a target sample by effective elimination or reduction of oxygen utilizing an oxygen scavenging system that creates an oxygen depleted environment conducive for the selective enrichment and detection of anaerobic or microaerophilic microorganisms in a target sample.

Advantageously, the present invention provides a quick, simple and convenient method for successful cultivation of anaerobes and/or microaerophiles by the addition of an enzyme-substrate system to a liquid medium and sample suspected of containing an anaerobe or a microaerophile in a container, wherein said enzyme-substrate system upon activation by hydration reduces or eliminates the dissolved oxygen making the detection and/or enrichment of anaerobic and/or microaerophilic organisms in the sample convenient and substantially easier than conventional means.

Advantageously, the present disclosure provides a process for culturing anaerobes and/or microaerophiles which does not require special or costly procedures for producing and maintaining anaerobic conditions and which, in fact, may be cultured conveniently and economically in ordinary incubators on a large, commercial scale. Moreover, unlike conventional techniques (e.g., anaerobic glove box, GASPAK gas generating pouches) for culturing anaerobic microorganisms the inventive method described herein removes oxygen directly from the liquid culture media, rather than removing it from the atmosphere in which the culture medium is held.

In addition, the present disclosure provides a method for easy detection of anaerobes and/or microaerophiles which advantageously is accomplished in a simpler, more economical, efficient and convenient manner.

Even further, the present disclosure advantageously provides a method for detecting anaerobic and/or microaerophilic microorganisms by creating an substantially oxygen depleted environment using an oxygen scavenging system comprising an enzyme of an oxidoreductase family and its substrate thereof, thus creating conditions conducive for the enrichment of said microorganisms.

Accordingly, in one aspect, the present disclosure provides a method. The method can comprise forming an aqueous mixture in a container; the mixture comprising a sample containing an anaerobic microorganism or a microaerophilic microorganism, a predefined volume of a medium that supports growth of said anaerobic or microaerophilic microorganism, and an oxygen scavenging system. The oxygen scavenging system can comprise effective amounts of i) an enzyme of an oxidoreductase family and ii) a substrate for said enzyme. The oxygen scavenging system can be activated upon hydration thereby depleting dissolved oxygen in the medium to a concentration that facilitates growth of an anaerobic microorganism or a microaerophilic microorganism. The enzyme can be selected from a group consisting of ascorbic acid oxidase and laccase. The method further can comprise incubating the aqueous mixture under conditions to facilitate at least one cell division of said anaerobic microorganism or microaerophilic microorganism. In any embodiment, the method further can comprise detecting growth of the anaerobic microorganism or the microaerophilic microorganism. In any embodiment, detecting growth of the microorganism can comprise analyzing the anaerobic microorganism or microaerophilic microorganism to associate the anaerobic microorganism or microaerophilic microorganism with a genus, a species, or a group of microorganisms characterized by a feature other than its ability to grow in an oxygen-containing environment.

In another aspect, the present disclosure provides a culture system for culturing a microaerophilic microorganism or an anaerobic microorganism. The system can comprise effective amounts of i) an enzyme of an oxidoreductase family and ii) a substrate for said enzyme, a container, and a predetermined volume of aqueous medium that supports growth of said anaerobic or microaerophilic microorganism.

The enzyme can be selected from a group consisting of ascorbic acid oxidase and laccase. The effective amounts can be effective to deplete dissolved oxygen in the predetermined volume to a concentration that facilitates growth of a microaerophilic microorganism or an obligately-anaerobic microorganism. In any embodiment, the container can be substantially impermeable to oxygen.

In yet another aspect, the present disclosure provides a kit. The kit can comprise a sealable container and an oxygen scavenging system comprising effective amounts of i) an enzyme of an oxidoreductase family and ii) a substrate for said enzyme. The enzyme can be selected from a group consisting of ascorbic acid oxidase and laccase. In any embodiment, the effective amounts are effective to deplete the dissolved oxygen in the predefined volume to about 100 µM or less, about 10 µM or less, about 1 µM or less, 0.1 µM or less, or 0.01 µM or less. In any embodiment, the effective amounts are effective to deplete the dissolved oxygen in the predefined volume to the concentration that facilitates the growth in about 60 minutes or less.

In any of the above embodiments, the oxygen scavenging system of the present invention upon activation creates an environment that is substantially depleted of oxygen or contains traces of oxygen to facilitate the culture of obligate anaerobes or microaerophiles, respectively.

In any of the above embodiments of the present invention, the oxygen scavenging system upon activation allows for the selective enrichment of anaerobic and/or microaerophilic microorganisms contained in a target sample.

In any of the above embodiments, the container can be a container that is substantially impermeable to oxygen.

The features and advantages of the present invention will be understood upon consideration of the detailed description of the preferred embodiment as well as the appended claims. These and other features and advantages of the invention may be described below in connection with various illustrative embodiments of the invention.

The above summary of the present invention is not intended to describe each disclosed embodiment or every implementation of the present invention. The detailed description which follows more particularly exemplifies illustrative embodiments. Other features, objects and advantages will become apparent from the description and from the claims.

DETAILED DESCRIPTION

The present invention will now be described more fully herein after. For the purposes of the following detailed description, it is to be understood that the invention may assume various alternative variations and step sequences, except where expressly specified to the contrary. Thus, before describing the present invention in detail, it is to be understood that this invention is not limited to particularly exemplified systems or embodiments that may of course, vary. The use of examples anywhere in this specification including examples of any terms discussed herein is illustrative only, and in no way limits the scope and meaning of the invention or of any exemplified term. Likewise, the invention is not limited to various embodiments given in this specification.

As used herein, the singular forms "a," "an," and "the" include plural reference unless the context clearly dictates otherwise. The term "and/or" means one or all of the listed elements or a combination of any two or more of the listed elements.

The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

When the term "about" is used in describing a value or an endpoint of a range, the disclosure should be understood to include both the specific value or end-point referred to.

As used herein the terms "comprises", "comprising", "includes", "including", "containing", "characterized by", "having" or any other variation thereof, are intended to cover a non-exclusive inclusion.

The term "microorganism" or "microbe" as used herein refers to any microscopic organism, which may be a single cell or multicellular organism. The term is generally used to refer to any prokaryotic or eukaryotic microscopic organism capable of growing and reproducing in a suitable culture medium, including without limitation, one or more of bacteria. Microorganisms encompassed by the scope of the present invention include prokaryotes, namely the bacteria and archaea; and various forms of eukaryotes, comprising the protozoa, fungi, yeast (e.g., anaerobic yeast), algae etc. The term "target microorganism" refers any microorganism that is desired to be detected.

The term "anaerobic microorganism" or "anaerobe" as used herein refers to microorganisms which are sensitive to oxygen and will not grow in the presence of oxygen. An anaerobic microorganism or anaerobe is any organism that does not require oxygen for growth. Anaerobic microorganisms include both obligate anaerobes and facultative anaerobes. Obligate anaerobes are those microorganisms which will die when exposed to atmospheric levels of oxygen. A facultative anaerobe is an organism that can carry out aerobic respiration if oxygen is present, but is capable of switching to fermentation or anaerobic respiration if oxygen is absent. Methods and systems of the present invention could be used for the enrichment and detection of both obligate anaerobes and facultative anaerobes.

The term "microaerophilic microorganism" or "microaerophiles" is used herein to refer to any microorganism which grows only in the presence of micro quantities of oxygen. Microaerophiles use oxygen, but only at very low concentrations (low micromolar range), typically oxygen concentration levels of 5-15% with growth inhibited by normal oxygen concentrations or concentrations greater than about 15%.

The term "culture" or "growth" of microorganisms as used herein refers to the method of multiplying microbial organisms by letting them reproduce in predetermined culture media under conditions conducive for their growth. More particularly it is the method of providing a suitable culture medium and conditions to facilitate at least one cell division of a microorganism. Culture media are solid, semi-solid or liquid media containing all of the nutrients and necessary physical growth parameters necessary for microbial growth.

The term "enrichment" as used herein refers to the culture method of selectively enriching the growth of a specific microorganism by providing medium and conditions with specific and known attributes that favors the growth of that particular microorganism. The enrichment culture's environment will support the growth of a selected microorganism, while inhibiting the growth of others.

"Oxygen scavenger", "oxygen scavenging system", "enzyme-substrate system" will be used broadly herein to refer to a system which can consume, deplete or react with oxygen from a given environment. Preferably, the oxygen scavenging system comprises an enzyme-substrate system comprising effective amounts of an enzyme of an oxidoreductase family and a substrate for said enzyme and is capable of actively removing oxygen from a given environment upon activation.

The term "activation" or "activated" refer to a state wherein the oxygen scavenging system is capable of scavenging oxygen, as described in the invention herein. According to the present invention, the process of activation which brings about the catalytic function of the enzyme typically through hydration. Preferably, in accordance with the present invention the hydration is effected through contact with the liquid medium or sample.

The terms "inactivation" or "inactivated" refer to a state the oxygen scavenging system is not capable of scavenging oxygen. The oxygen scavenging system is typically maintained in an "inactive" state until a point proximate, or coincident with, the addition of the microorganism-containing sample into the medium, in order to preserve the enzymatic activity of the oxygen scavenging system and to prevent premature activation of said system prior to the commencement of oxygen scavenging in a target sample or medium.

The minimum components of the oxygen scavenging system comprise an enzyme capable of reducing molecular oxygen and an appropriate substrate for said enzyme. Preferably, said system comprises an effective amount of an enzyme of an oxidoreductase family and its suitable substrate. More preferably, the enzyme substrate system that could be used in the present invention involves the use of an enzyme of an oxidoreductase family, the enzyme selected from the group consisting of ascorbate oxidase, laccase or their combinations thereof.

The terms "reducing substrate", "substrate" and "reductant" are used interchangeably herein and each refers to a substance that is capable of acting as a source of electrons for the enzyme included within the oxygen scavenging system of the invention.

The present disclosure generally relates to articles and methods for growing anaerobic or microaerophilic bacteria. In particular, the present disclosure provides a system for culturing anaerobic or microaerophilic bacteria. The system comprises effective amounts of an oxidoreductase enzyme that reduces molecular oxygen and a corresponding substrate that is oxidized in an oxygen-consuming reaction. Advantageously, the inventive system is highly stable (e.g., at ambient temperatures) and the system obviates the need for specialized equipment and/or compressed gases in order to achieve and maintain an anaerobic environment. In addition, the system is capable of creating a liquid environment that facilitates growth of an anaerobic or a microaerophilic microorganism less than one hour after the system is activated.

It has been largely known that the potential for bacterial contamination exists in products which are designed for human consumption or use. Manufacturers and/or processors of the products intended for human consumption generally test these products to ensure the quality and safety of the products for human consumption. Foods, pharmaceuticals, beverages, cosmetics, and water are routinely tested for microbial contamination with pathogenic microorganisms, including anaerobic and microaerophilic bacteria.

Classically, culture and enrichment of anaerobes has been extremely difficult owing to the need to exclude oxygen, slow growth and complex growth requirements. Anaerobic culture media are required to be maintained under completely oxygen free conditions and this necessitates adoption of cumbersome physical and chemical techniques. To this end, the screening, culture and laboratory maintenance of anaerobic bacteria requires specialized culture vessels, incubation equipment, media which render the process extremely labor intensive, expensive and time consuming Additionally, the operation of these devices also typically requires elaborate set up procedures necessitating skilled labor. For these reasons, routine testing of food/water or other biological samples for presence or absence of anaerobic microorganisms has become extremely cumbersome thereby discouraging their routine use.

Methods that have been traditionally employed for achieving anaerobiosis include, physical and chemical techniques like the use of the anaerobic chamber, exclusion of oxygen or production of vacuum, sparging technique involving the displacement of oxygen with other gases, use of reducing agents, absorption of oxygen by chemical or biological means and reduction of oxygen.

An anaerobic chamber is, for example, a plastic glove box that contains an atmosphere of $H_2$, $CO_2$, and $N_2$. Culture media are placed within the chamber by means of an air lock which can be evacuated and refilled with $N_2$.

Another conventional method of creating an anaerobic environment is by incubating the cultures in vacuum desiccators, but the large scale adaption of this method has been restricted owing to the inability to achieve complete anaerobiosis.

The traditional candle jar which relies on the principle of displacement of oxygen is yet another popular but ineffective method. The methodology employed includes placing the inoculated plates inside a large air tight container and a lighted candle kept in it before the lid is sealed. Although is normally expected that the burning candle will use up all the available oxygen before it gets extinguished, in practice traces of oxygen is always left behind.

Another method to remove oxygen from the liquid medium is by the addition of reducing agents. But most of these agents are strong reducing agents and any residual agent present in the medium tends to inhibit the subsequent growth of anaerobes in the medium.

Achieving anaerobiosis by other chemical means has been attempted employing mixture of chemicals; namely mixtures comprising pyrogallic acid/sodium hydroxide, mixtures comprising chromium/sulfuric acid, mixtures comprising sodium borohydride/cobalt chloride or mixtures comprising citric acid/sodium bicarbonate (e.g., as in a GASPAK gas generating pouch system), whereby hydrogen gas and carbon dioxide are produced. Hydrogen then reacts with oxygen gas on a palladium catalyst to produce more water, thereby removing oxygen gas. Some of the frequently encountered drawbacks that limit the use of such chemical methods include release of carbon monoxide which may inhibit the growth of some bacteria sensitive to these gases. Yet another limitation particularly in employing a GASPAK gas generating pouch system is the generation and management of large volumes of water formed during the catalytic reaction.

Sparging liquid media with high purity nitrogen or other inert gas effectively removes oxygen from liquid medium. But this method often causes foaming of liquid media and associated mechanical problems. Moreover after sparging is stopped, the medium is easily recontaminated with oxygen.

Modern anaerobic laboratories still use adaptations of this technique in the form of gassing stations. But gassing stations are not commercially available and have to be custom made. This poses great challenge with respect to cost and time.

It is clear that conventional methods necessitate the use of relatively expensive equipment along with the expenditure of large amounts of time, labor and skill, however are mostly ineffective in achieving complete anaerobiosis.

L-ascorbic acid oxidase/ascorbate oxidase enzyme is a multi-copper enzyme belonging to the family of oxidoreductases (EC 1.10.3.3) that catalyzes the four-electron reduction of oxygen to water with the concomitant one-electron oxidation of a substrate (i.e., either ascorbate or ascorbic acid). This enzyme catalyzes chemical reactions that include, but are not limited to, the reactants ("substrates") and products shown in the following exemplary reaction:

$$2\text{L-ascorbate} + O_2 \rightleftharpoons 2\text{dehydroascorbate} + 2H_2O.$$

Thus, the two substrates of L-ascorbic acid oxidase/ascorbate oxidase enzyme in the exemplary reaction are L-ascorbate and $O_2$, whereas its two respective products are dehydroascorbate and $H_2O$.

In any embodiment, the substrate for ascorbate oxidase comprises ascorbic acid and its salts thereof, particularly alkali metal salts. In the present invention, examples of an ascorbic acid compound include L-ascorbic acid, sodium L-ascorbate, calcium L-ascorbate and sodium D-iso-ascorbate, and they may be used singly or in the form of a mixture thereof. Ascorbic acid oxidase is known to catalyze oxygen-consuming reactions with ascorbic acid derivatives and salts thereof, as well as with non-ascorbate substrates. Non-limiting examples of ascorbic acid derivatives include D-iso-ascorbate, D-araboascorbic acid, 6-amino-L-ascorbate, 6-deoxy-L-ascorbate, D-erythroascorbate, 6-O-phenyl-L-ascorbate, and 6-S-phenyl-L-ascorbate. Non-limiting examples of non-ascorbate substrates may include hydroquinone, pyrogallol, catechol and the like. The terms "ascorbic acid" and "ascorbate" will be used interchangeably herein to refer to both ascorbic acid and salts thereof.

The laccase enzyme refers to a multi-copper oxidoreductase enzyme (EC 1.10.3.2) that catalyzes the four-electron reduction of oxygen to water with the concomitant one-electron oxidation of a substrate.

Laccase is known to oxidize a wide range of phenolic molecules, as well as some small non-phenolic molecules. Accordingly, suitable substrates for use with laccase in an oxygen-scavenging system of the present disclosure include, but are not limited to, phenols, L-tyrosine, o-diphenol and p-diphenol.

In one aspect, the present disclosure provides a system for the culture of a microaerophilic microorganism or an anaerobic microorganism. In any embodiment, said system may comprise an effective amount of an enzyme of an oxidoreductase family and a substrate for said enzyme and said enzyme and substrate system gets activated upon hydration by contact with the liquid medium thereby creating an aqueous environment substantially depleted of oxygen; conducive for the growth of anaerobic or microaerophilic microorganism. In any embodiment, an aqueous environment that is "substantially depleted of oxygen", as used herein, refers to an aqueous environment (e.g., an aqueous buffer or culture medium) that, after activation of the enzyme and substrate system in the aqueous environment, comprises less than 50% of the dissolved oxygen that was present in the aqueous environment before activating the enzyme and substrate system.

A well-mixed aqueous liquid that is saturated with air comprises about 470 µM dissolved oxygen at 30° C. R. A. Ludwig ("Mesophilic bacteria transduce energy via oxidative metabolic gearing", Research In Microbiology, vol. 155 (2004), pp. 61-70) discloses the rate of metabolic activity of aerobic microorganisms decreases significantly at concentrations of dissolved oxygen below about 10 µM and essentially ceases at concentrations of dissolved oxygen below about 0.2 µM. In contrast, Ludwig discloses that microaerophilic microorganisms exhibit metabolic activity in environments having dissolved oxygen concentrations ranging from about 0.001 µM to about 200 µM with the highest metabolic activity in environments having dissolved oxygen concentrations ranging from about 0.05 µM to about 10 µM. In addition, Ludwig discloses strictly-anaerobic microorganisms exhibit the highest rate of metabolic activity in environments having dissolved oxygen concentrations less than or equal to about 0.005 µM. The metabolic activity of strict anaerobes essentially ceases in environments having dissolved oxygen concentrations greater than about 0.2 µM.

A person having ordinary skill in the art will recognize dissolved oxygen can be measured in an aqueous liquid using a variety of techniques known in the art including, for example, a dissolved oxygen meter and probe.

In any embodiment of a method used to enrich a microaerophilic microorganism and/or an anaerobic microorganism, an aqueous environment that is "substantially depleted of oxygen", as used herein, refers to an aqueous environment (e.g., an aqueous buffer or culture medium) that; after activation of the enzyme and substrate system in the aqueous environment; has a dissolved oxygen concentration less than or equal to about 100 µM, less than or equal to about 50 µM, less than or equal to about 10 µM, less than or equal to about 5 µM, less than or equal to about 1 µM less than or equal to about 0.5 µM, less than or equal to about 0.1 µM, less than or equal to about 0.05 µM, less than or equal to about 0.01 µM, or less than or equal to about 0.005 µM.

The method, system or kit of the present disclosure can be used to favor growth of a microaerophilic microorganism over growth of an aerobic microorganism. Accordingly, in any embodiment of a method of enriching and/or detecting a microaerophilic microorganism according to the present disclosure, substantially depleting the oxygen in a culture medium can comprise depleting the dissolved oxygen to a concentration between about 0.01 µM and about 10 µM. In any embodiment of a method of enriching and/or detecting a microaerophilic microorganism according to the present disclosure, substantially depleting the oxygen in a culture medium can comprise depleting the dissolved oxygen to a concentration between about 0.01 µM and about 1 µM. In any embodiment of a method of enriching and/or detecting a microaerophilic microorganism according to the present disclosure, substantially depleting the oxygen in a culture medium can comprise depleting the dissolved oxygen to a concentration between about 0.1 µM and about 1 µM.

The method, system or kit of the present disclosure can be used to favor growth of a microaerophilic microorganism over growth of an anaerobic microorganism. Accordingly, in any embodiment of a method of enriching and/or detecting a microaerophilic microorganism according to the present disclosure, substantially depleting the oxygen in a culture medium can comprise depleting the dissolved oxygen to a concentration between about 0.05 µM and about 100 µM. In any embodiment of a method of enriching and/or detecting a microaerophilic microorganism according to the present disclosure, substantially depleting the oxygen in a culture medium can comprise depleting the dissolved oxygen to a concentration between about 0.01 µM and about 100 µM. In any embodiment of a method of enriching and/or detecting a microaerophilic microorganism according to the present disclosure, substantially depleting the oxygen in a culture medium can comprise depleting the dissolved oxygen to a concentration between about 0.5 µM and about 100 µM. In any embodiment of a method of enriching and/or detecting a microaerophilic microorganism according to the present disclosure, substantially depleting the oxygen in a culture medium can comprise depleting the dissolved oxygen to a concentration between about 1 µM and about 100 µM.

The method, system or kit of the present disclosure can be used to favor growth of a strict anaerobic microorganism over growth of a microaerophilic microorganism. Accordingly, in any embodiment of a method of enriching and/or detecting an anaerobic microorganism according to the present disclosure, substantially depleting the oxygen in a culture medium can comprise depleting the dissolved oxygen to a concentration about 0.2 µM or lower. In any embodiment of a method of enriching and/or detecting an anaerobic microorganism according to the present disclosure, substantially depleting the oxygen in a culture medium can comprise depleting the dissolved oxygen to a concentration about 0.1 µM or lower. In any embodiment of a method of enriching and/or detecting an anaerobic microorganism according to the present disclosure, substantially depleting the oxygen in a culture medium can comprise depleting the dissolved oxygen to a concentration about 0.05 µM or lower. In any embodiment of a method of enriching and/or detecting an anaerobic microorganism according to the present disclosure, substantially depleting the oxygen in a culture medium can comprise depleting the dissolved oxygen to a concentration about 0.01 µM or lower.

In any embodiment of a method or system of the present disclosure, the term "effective amount" should be understood as meaning an amount of enzyme and/or enzyme substrate effective in achieving an oxygen scavenging effect that reduces the concentration of dissolved oxygen in a given volume of aqueous medium to an extent that permits growth of a microaerophilic microorganism or an anaerobic microorganism for a sufficient period of time, optionally to facilitate detection of the microorganism.

The amount of enzyme employed in the oxygen-scavenging system may depend on a number of factors such as, for example, the sample volume, the initial concentration of oxygen, the desired concentration of oxygen required in a given environment (e.g., to facilitate growth of an obligate anaerobe versus a microaerophilic microorganism), the desired rate of scavenging (e.g., to minimize exposure of obligate anaerobes to potentially-lethal concentrations of oxygen), rate of oxygen ingress (e.g., if the container is not impermeable to oxygen), and the specific activity of the enzyme employed. In any embodiment, however, after forming the aqueous mixture using the method of the present disclosure, the enzyme may be present in the mixture in an amount of at least 1K Unit/L (1000 units/L), or in some cases at least 2K Unit/L (2000 units/L), or in some cases at least 3K Unit/L (3000 units/L), or in some cases at least 4K Unit/L (4000 units/L). In order to facilitate rapid depletion of dissolved oxygen in an aqueous culture medium, after forming the aqueous mixture, the enzyme may be present in the mixture in an amount of at least 4K Unit/L of the total volume of the liquid medium.

The amount of enzyme substrate employed in the oxygen-scavenging system can also affect the rate, extent, and duration of oxygen depletion from a given environment in a container of the present disclosure. Accordingly, in any embodiment, after forming the aqueous mixture using the method of the present disclosure, the substrate is present in the mixture may be about 0.1 to 100 mg/ml. In any embodiment, the concentration of the enzyme substrate in the aqueous mixture of the present disclosure may be about 0.1 to 50 mg/ml. In any embodiment, the concentration of the enzyme substrate in the aqueous mixture of the present disclosure may be about 0.1 to 10 mg/ml. In any embodiment, the concentration of the enzyme substrate in the aqueous mixture of the present disclosure may be about 0.1 to 5 mg/ml. A person skilled in art would appreciate that the amount of substrate may be varied depending upon the desired rate of scavenging to be achieved or desired concentration of oxygen to be obtained in a given volume of the liquid medium depending on the nature of the target microorganism to be enriched.

It is well known that hydration is necessary for enzyme catalytic function and that dry enzymes are nonfunctional. Hydration may facilitate catalytic function and/or the diffusion of substrate and product. Accordingly the enzyme substrate system as per the present invention is activated upon contact with sufficient moisture; and below a threshold hydration level, enzyme substrate system is substantially inactive. The term "oxygen scavenging system" as used herein refers to both the activated or inactivated system. Accordingly as per the invention the enzyme-substrate system could be deployed in a variety of formats such as a tablet form (pills, donuts, or small spheres), lyophilized form, a sachet, a spray coating inside the container, dissolvable or degradable (e.g., degradable upon contact with an aqueous solution) pouches or capsules, or in powdered quick-dissolve media.

In any embodiment, it is contemplated that the enzyme or enzyme substrate of the system of the present disclosure can be deployed as an agglomerated powder. Optionally, the enzyme or enzyme substrate can be agglomerated with one or more nutrients (e.g., broth nutrients or powdered nutrients) of a culture medium (e.g., an enrichment broth culture medium) as disclosed in PCT Publication No. WO2014/025514; which is incorporated herein by reference in its entirety.

In accordance to one aspect of the invention, the enzyme and substrate may be incorporated in to the liquid medium after the sterilization of the medium. As per another aspect, the enzyme or enzyme-substrate may be added concomitantly with the sample containing the microorganism into the medium. In another embodiment, the enzyme-substrate may be added after the addition of the sample. In any embodiment, the medium and the sample may be added to the enzyme substrate system which has been coated on the container wall.

The present disclosure is generally directed to a method for culturing and/or detecting anaerobic/microaerophilic microorganisms in a sample. The sample can be obtained from a variety of sources. In any embodiment, the source may be a food source (e.g., a food ingredient, an in-process food sample, or a finished-product food sample). In some embodiments, the source may be a non-food source. In contrast to conventional methods for detecting anaerobic/microaerophilic microorganisms, which require laborious procedures, the inventive method effortlessly allows the user to merely combine the sample with a predefined medium and an oxygen-scavenging system in accordance with the invention to create conditions conducive for the enrichment and detection of anaerobic/microaerophilic microorganisms.

According to one embodiment, a sample to be tested may comprise providing a sample that is suspected of containing a target anaerobic/microaerophilic microorganism. Non-limiting examples of suitable samples include food samples, namely variety of food, beverage or food- or beverage-processing environmental sources. Non-limiting examples of such food sources include raw or processed fruits or vegetables, raw or processed meat, non-fluid or fluid based dairy products, syrups, fermented beverages, potable water, milk and the like. Pasteurized food or beverages may also form suitable sources. Examples also include, but are not limited to, meats, poultry, eggs, fish, seafood, vegetables, fruits, prepared foods (e.g., soups, sauces, pastes), grain products (e.g., flour, cereals, breads), canned foods, milk, other dairy products (e.g., cheese, yogurt, sour cream), fats, oils, desserts, condiments, spices, pastas, beverages, water, animal feed, other suitable comestible materials, and combinations thereof.

The term "food" refers to a solid or liquid source (e.g., including, but not limited to, solutions, dispersions, emulsions, suspensions, etc., and combinations thereof) and/or semisolid comestible composition.

Suitable samples to be used in a method of the present disclosure also include clinical samples derived from a variety of human/animal sources such as physiological fluid, for instance, blood, saliva, synovial fluid, pus, sweat, cerebrospinal fluid, urine, lactation milk, exudates, nasal sample, bile, bone marrow, direct lung aspirate, tissue biopsy from a normally sterile site, fluid from a normally sterile site (like a joint), dental abscess, abdominal or pelvic abscess, a wound (e.g., a traumatic or surgical wound), a severe burn as well as other possible infected tissues and the like. In any embodiment, a sample to be tested may comprise a biological tissue and/or a biological fluid.

Suitable samples to be used in a method of the present disclosure also include environmental samples (e.g., environmental water samples (e.g., surface water, process water), soil samples, surface residue samples, and the like).

Various sampling techniques may be employed for the collection of the sample suspected of containing a target anaerobic and/or microaerophilic microorganism. Such sampling techniques are suitable for the methods of the present invention as well. The test sample (e.g., liquid) may be subjected to treatment prior to screening, such as for instance, this may include concentration, precipitation, filtration, centrifugation, dialysis, dilution and the like. In any embodiment, one or more various dilutions of the sample may be prepared and each of the dilutions may be used as inoculum.

In another aspect the present disclosure provides a method for reducing and/or removing oxygen comprising: a) providing a container to contain a target sample suspected of containing an anaerobic and/or microaerophilic microorganism; b) providing an oxygen scavenging system comprising: a) an effective amount of enzyme of an oxidoreductase family; and b) an effective amount of a reducing substrate and c) contacting the contents of the container with the oxygen scavenging system whereby oxygen is either reduced or removed from the sealed container thereby promoting the enrichment and/or detection of the anaerobic and/or microaerophilic microorganism. In any embodiment, the container may be a sealed container. Advantageously, a sealed container permits less ingress of oxygen from the ambient atmosphere after the oxygen scavenging system is activated.

In any embodiment, the present invention provides a method for culturing anaerobic and/or microaerophilic microorganisms comprising forming an aqueous mixture in a container; the mixture comprising a sample containing an anaerobic microorganism, predefined volume of a medium that supports growth of said anaerobic or microaerophilic microorganisms, and an oxygen scavenging system; wherein said oxygen scavenging system comprises effective amounts of i) an enzyme of an oxidoreductase family and ii) a substrate for said enzyme wherein said oxygen scavenging system being activated upon hydration thereby creating an aqueous environment substantially depleted of oxygen; and incubating the sample, medium, and oxygen-scavenging system under conditions to facilitate at least one cell division of said anaerobic microorganism. In any embodiment, the container may be a container that is substantially impermeable to oxygen. In any embodiment, the container may be a sealed container. Advantageously, a sealed container permits less ingress of oxygen from the ambient atmosphere after the oxygen scavenging system is activated.

According to another preferred embodiment, the present disclosure provides a method for detecting an anaerobic and/or microaerophilic microorganism in a sample. Accordingly, the instant disclosure provides a method of detecting an anaerobic and/or microaerophilic microorganism in a sample, the method comprising: contacting in a container, a predefined volume of aqueous liquid comprising: a sample suspected of containing an anaerobic microorganism, a medium that supports growth of said anaerobic and/or microaerophilic microorganism, and an oxygen scavenging system; wherein said oxygen scavenging system comprises an enzyme of an oxidoreductase family and a substrate for said enzyme; wherein said oxygen scavenging system being activated upon hydration thereby creating an aqueous environment substantially depleted of oxygen; incubating the sample, medium, and oxygen-scavenging system under conditions to facilitate at least one cell division of said anaerobic and/or microaerophilic microorganism; and detecting a presence or absence of said anaerobic and/or microaerophilic microorganism. In any embodiment, the container may be a container that is substantially impermeable to oxygen. In any embodiment, the container may be a sealed container. Advantageously, a sealed container permits less ingress of oxygen from the ambient atmosphere after the oxygen scavenging system is activated.

Accordingly the present disclosure provides a system for the culture of a microaerophilic and/or or anaerobic microorganism[s] said system comprising: effective amounts of i) an enzyme of an oxidoreductase family and ii) a substrate for said enzyme, said enzyme and substrate being activated upon hydration thereby creating an environment devoid of oxygen or containing traces of oxygen; a container; and a predetermined volume of aqueous medium that supports growth of said anaerobic or microaerophilic microorganism. In any embodiment, the container can be substantially impermeable to oxygen.

The term "container" or "package" refers to an object that forms an enclosure defining an interior space designed to hold a target sample of any type and that is having oxygen barrier properties. The terms "sealed container" and "sealed package" refer to a vessel that defines an interior space designed to contain the aqueous medium, target sample and oxygen scavenging system wherein said vessel is designed to substantially prevent unobstructed communication with the ambient atmosphere existing outside the vessel. The container may be in the form of a pouch, an envelope, a sealed wrapping, a bag, a can, a jar, a barrel, a box or a barrier bag, a zippered storage bag (e.g., a ZIPLOC storage bag) or the like, a lab blender bag (e.g., a STOMACHER bag), a flask with a stopper or a septum, a bottle with a stopper or a septum, or any form of sealed containment suitable for containment and growth of a microbial culture in aqueous medium. In any embodiment, the container may be sealable and, optionally, resealable.

The container may take any suitable shape or size for holding and containing a defined volume of medium and/or sample suspected of containing an anaerobic and/or microaerophilic microorganism. Furthermore, the container may be devoid of a suitable nutrient media or a nutrient media may be included within container. The container or package may be a single-use, disposable type of a container. Alternatively, the container or package may be reusable. In any embodiment, the container may be sterilized using processes that are known in the art for the particular material from which the container is made.

In any embodiment, the container may be made of substances which are substantially impermeable to oxygen, so that the influx of oxygen through the container wall does not substantially overwhelm the capacity of the oxygen scavenging system to deplete and/or maintain the oxygen in an aqueous medium in the container to a concentration that supports growth of an anaerobic or microaerophilic microorganism.

In any embodiment, the container may comprise a sealable port (e.g., a pierceable, self-sealing septum) for adding the sample or a reagent, for example. Additionally, or alternatively, the sealable port may be used to remove material (e.g., a portion or all of the aqueous mixture of the present disclosure, a portion or all of any gas (e.g., air) that was introduced into the container, and/or a reagent (e.g., the enzyme or enzyme substrate of the present disclosure)).

In any embodiment, the container may be made of a polymeric material. Preferably, a polymeric material that is substantially inert to the oxygen scavenging system and the contents of the sealed container. In any embodiment, the polymeric material can have a thickness and composition that renders it substantial impermeability to oxygen. Non-limiting examples of suitable polymeric materials include polyvinyl chloride, polyethylene, polycarbonate, polystyrene, polyvinyledene chloride (PVdC), ethylene vinyl acetate copolymers, polyvinylidene chloride copolymer, ethylene vinyl alcohol copolymer, polyamide (such as Nylon 6), polyacrylonitriles, polymethacrylonitrile, cellulose acetate, cellulose acetate butyrate, cellulose diacetate, Neoprene®, Teflon®, polysiloxane or mixtures or laminates thereof. In any embodiment, the container may be made of glass.

In any embodiment, the conatiner may be a multi-layer polymeric film laminate. In any embodiment, a container comprising a polymeric film may comprise an oriented polymeric film (e.g., oriented polypropylene (OPP), oriented nylon, oriented polyethylene terephthalate (OPET). In any embodiment, a container comprising a polymeric film may comprise a metalized film (e.g., a polymeric film having a metal (e.g., aluminum) coating. In any embodiment, a container comprising a polymeric film may comprise PVdC, PVdC copolymer or polyvinyl alcohol (PVOH) coated film (for example PVOH coated OPP, PVdC coated OPET, PVdC copolymer coated OPET, PVdC coated OPP, PVdC copolymer coated OPP).

The oxygen permeability of the container is influenced by the composition and thickness of the container. In any embodiment, it may be preferred to use a highly-flexible container (e.g., a bag fabricated by sealing one or more polymeric film along at least one edge) so as to minimize storage space and/or fit into a variety of differently-sized or shaped spaces for incubation. Alternatively, in any embodiment, it may be preferred to use a relatively rigid container (e.g., a glass bottle or tube. The oxygen permeability of any container can be measured as a rate of ingress or egress of oxygen through the walls of the container. The units are reported as nmol/(meters×seconds×Gpa).

In any embodiment, the oxygen permeability of the walls of the container can be less than about 100 nmol/(m×s×Gpa), for example. In any embodiment, the oxygen permeability of the walls of the container can be less than or equal to 50 nmol/(m×s×Gpa) less than or equal to 25 nmol/(m×s×Gpa), less than or equal to 15 nmol/(m×s×Gpa), or less than or equal to 10 nmol/(m×s×Gpa). By way of example, in any embodiment, the container may be constructed of a polyethylene terephthalate film having a thickness of about 0.025 mm and an oxygen permeability of about 6-8 nmol/(m×s×Gpa).

In any embodiment the container may be sealed. Although it may be preferred in some embodiments, residual air in the container need not be completely removed before or after sealing the container. Accordingly, in any embodiment, the sealed container, with the aqueous medium, the sample, and/or the oxygen-scavenging system disposed therein may include a headspace. The headspace can comprise a gas (e.g., ambient air) that is trapped in the container when the container is sealed. Preferably, the headspace is relatively small, so as not to constitute a significant reservoir of oxygen present in the sealed container. In any embodiment, the headspace volume may be about 0 milliliters to about 50 milliliters. In any embodiment of a method of the present disclosure, air in the headspace may be completely expelled, at least partially expelled, or it may not be removed at all.

Present invention provides a method for detecting the presence of anaerobic microorganism and/or microaerophilic microorganism in samples. In addition, a sample may comprise higher (e.g., at least 2-times higher, at least 3-times higher, at least 5-times higher, at least 10-times higher, at least 100-times higher, at least 1000-times higher, at least 10000-times higher, at least 100000-times higher) concentrations of aerobic microorganisms, relative to the concentration of microaerophilic or anaerobic microorganisms. Where the microorganism to be detected (i.e., "target microorganism") is relatively scarce in the sample, or are in fact in very low numbers, an enrichment of said microorganism in the sample may be required in order to detect it. Advantageously, the method of the present disclosure promotes enrichment of anaerobic or microaerophilic microorganisms in a mixed microbial population comprising an aerobic microorganism and at least one of a microaerophilic microorganism or an anaerobic microorganism.

Non-limiting examples of typical anaerobic bacteria which may be detected by a method or system according to the present disclosure include *Bacteroides, Fusobacterium, Porphyromonas, Prevotella, Actinomyces, Bifidobacterium, Clostridium, Peptostreptococcus, Propionibacterium, Lactobacillus, Peptococcus, Peptostreptococcus* and *Veillonella*. Some of the commonly occurring food contaminating anaerobic bacteria which could be readily detected by the present invention comprises bacteria of *Clostridium* sp. viz., *Clostridium perfringens, Clostridium sporogenes, C. botulinum*, and *C. difficile* which can cause food poisoning.

The method or system of the present disclosure may be used for the detection and culture of the microaerophilic bacteria. Non-limiting examples of microaerophilic organisms in accordance with the invention are of the genus *Campylobater, Borrelia* and *Helicobacter*. For example, the method or system present disclosure could be used for the detection of *Campylobacter jejuni* and *Campylobacter coli* which are two major species that cause food poisoning. *Campylobacter* spp. most commonly occurs as food contaminants and they are known to grow poorly in ordinary anaerobic culture. These organisms typically require oxygen in an amount of 5-15% for growth.

In any embodiment, the method or system of the present disclosure may be used for the detection and culture of the facultative anaerobes. Non-limiting examples of typical facultative anaerobes that may be detected by the present invention include bacteria selected the genus *Staphylococcus, Streptococcus, Escherichia, Listeria* and *Shewanella*.

The culture medium as herein described may be selected from the group consisting of a nutrient medium, a selective medium, an enriched medium and an enrichment medium. Preferably, the medium is particularly suitable for the growth, isolation and/or identification of anaerobes and/or microaerophiles. A suitable medium for the culture of a target anaerobic and/or microaerophilic organism typically may contain as the carbon source, one or more of glucose, fructose, galactose, sucrose, lactose, cellobiose, maltose, xylose, ribose, mannose, trehalose, cellubiose, arabinose, starch hydrolysate or suitable carbohydrate sources. The suitable medium further may comprise a proteinaceous material or components thereof (e.g., one or more amino acid, one or more oligopeptides). The proteinaceous material is desirably introduced in amounts between about 2 to 25% and may comprise any suitable source such as vegetable protein meals as, for example, peptones, soy bean meal, or animal proteins as, for example, fishmeal, livermeal, meat meal, and the like. Optional salts to be incorporated into the medium can be selected from sodium carbonate, potassium sulphate, calcium chloride, magnesium chloride, ferrous sulphate, ferrous sulphate heptahydrate, magnesium sulphate or their mixtures thereof. Water is added to the mixture of solid nutrients and substrate, desirably in amount comprising about 25% to 75% by weight. Nonlimiting examples of enrichment culture media include, for example Bolton's broth, selenite broth, and cooked-meat broth. The pH of the medium may be adjusted to the optimum range for growth of the suspected species of bacteria. The medium may be sterilized before the addition of the oxygen scavenging system and the sample.

In any embodiment of the invention, the incorporation of the oxygen-scavenging system into the liquid medium may be such that the system gets activated simultaneously with the addition of the sample in which the presence of the anaerobe or microaerophile is to be detected. This circumstance facilitates efficient timing and duration of the oxygen scavenging reaction to achieve an appropriate level of anaerobiosis in the liquid medium.

In accordance with the present invention, incubation of the sample, medium and oxygen-scavenging system may be carried out at optimum conditions to facilitate at least one cell division of the anaerobic and/or microaerophilic organism to be enriched and/or detected.

The incubation temperature may be selected according to the microorganism to be detected. The incubation may be carried out at a temperature conducive for the growth of the anaerobic/microaerophile which may be suspected to be present in the sample. A person of ordinary skill in the art would select an appropriate incubation temperature (e.g., about 25° C., about 30° C., about 35° C., about 37° C., about 42° C.) based on the nature of microorganism suspected to be present in the target sample. Accordingly incubation temperature may depend on the optimal growth temperature of the suspected bacterium in the sample, for e.g. the optimal growth temperature of *Campylobater* species is between 37 and 42° C.; for *Clostridium* sp. about 37° C. For many of the human pathogen microorganisms the ideal temperature for incubation may be about 37° C.

The duration of incubation may vary depending on the microorganism to be enriched. The period of time may be a predetermined period of time. In some embodiments, incubating the aqueous mixture can comprise incubating the mixture at least about 1 hour, at least about 5 hours, at least about 8 hours, at least about 12 hours, at least about 18 hours, at least about 24 hours, at least about 48 hours, or at least about 72 hours. In some embodiments, the culture device can be incubated not more than about 24 hours, not more than about 48 hours, or not more than about 72 hours.

It is contemplated that a culture system or method of the present disclosure can be used to enrich sulfate-reducing bacteria. In these embodiments, it may be desired to incubate the aqueous mixture for up to about 28 days.

Although it is not required in a method of the present disclosure, incubating the aqueous mixture optionally may further comprise incubating the aqueous mixture with agitation (e.g., the container can be agitated during the incubation period using agitation means known in the art. Alternatively, the aqueous mixture can be incubated without agitation according to the method described in the Examples hereinbelow.

Advantageously, the method or system of the present disclosure provides for incubation of the medium inoculated with the sample containing anaerobic/microaerophilic bacteria in a regular incubator (i.e., an incubator having an ambient (i.e., oxygen-containing) gaseous environment). Use of the method in accordance with the present disclosure obviates the need for special equipment like an anaerobic chamber.

In any embodiment, a method of the present disclosure optionally includes a step of detecting growth of an anaerobic or microaerophilic microorganism in the container. In any embodiment, detecting growth of an anaerobic or microaerophilic microorganism can comprise observing growth (e.g., visually or by using an instrument such as a nephthelometer or spectrophotometer, for example). The observation may be conducted during and/or subsequent to the incubating step. In any embodiment, the observation of growth of the anaerobe and/or microaerophile can comprise observation of turbidity. Typically, bacterial suspensions having viable cell counts of approximately $1 \times 10^7$ or above will have a turbidity that can be observed. Observation of turbidity in the medium can indicate that enrichment of the anaerobe and/or microaerophile has occurred. Microbial growth may also be detected by using an indicator reagent and measuring an observable change in the indicator agent such as, for instance, a pH indicator reagent or a chromogenic or fluorogenic enzyme substrate in the medium after incubation.

In any embodiment, a method according to the present disclosure further can comprise analyzing the anaerobic microorganism or microaerophilic microorganism to associate the anaerobic microorganism or microaerophilic microorganism with a genus, a species, or a group of microorganisms characterized by a feature other than its ability to grow in an oxygen-containing environment. Analyzing the microorganism can be performed using any microorganism analysis method known in the art including, but not limited to biochemical methods (e.g., detection of en enzyme activity or biomolecule associated with a particular microorganism or group of microorganisms), genetic methods (e.g., nucleic acid amplification, nucleic acid hybridization, PCR, nucleic acid sequencing), and/or immunological methods (e.g., western blot, ELISA). In any embodiment, it may be desirable to detect a metabolic byproduct or a toxin associated with a particular microorganism or group of microorganisms.

In any embodiment, the method further can comprise contacting the mixture with a material that indicates the presence or absence of oxygen. In any embodiment, contacting the mixture with the material can comprise dissolving or suspending the material in the mixture. Thus, in any embodiment, the material may be soluble in water. Alternatively, the material may be insoluble in water or may be disposed, for example, in a polymer or a coating that is insoluble in water. For example, the material can be any suitable material that can be incorporated into the medium and/or sample to be tested and that indicates the presence or absence of oxygen in the given environment by means of a reversible or irreversible color change. Thus, the indicator may have one color in the presence of oxygen and a different color in an atmosphere which is substantially depleted and/or devoid of oxygen. Also, the indicator may be colorless when no oxygen is present and develop a color when oxygen is present, or the indicator may be colorless when oxygen is present and develop a color when little or no oxygen is present in the surrounding atmosphere. In any embodiment, the indicator may include a fluorescent indicator reagent. Suitable indicator reagents include, but are not limited to, oxygen-sensitive dyes that are known in the art.

A non-limiting example of a water-soluble, reversible color indicator which may be employed in a method or system of the present disclosure is methylene blue. Methylene blue is colorless in the absence of oxygen but in the presence of sufficient dissolved oxygen, such as in air-equilibrated aqueous liquids for example, it has a blue color. In any embodiment, the color indicating material may be one that undergoes a reversible color change such that any change from an oxygen-containing atmosphere to an atmosphere substantially depleted and/or devoid of oxygen, or from an atmosphere devoid of oxygen to one containing oxygen, will be indicated by the color change.

In any embodiment, after incubating the mixture under conditions to facilitate at least one cell division, the method optionally can comprise identifying and/or enumerating microorganisms in the mixture. Microorganisms can be identified using any suitable method known in the art (e.g., biochemical identification, genetic identification, immunologic identification). Enumerating microorganisms in the mixture can comprise, for example, plating and counting the organism on agar after they've grown in their enrichment. In any embodiment, the mixture, or a portion thereof, can be purified (e.g., to remove substances that may otherwise interfere with the identification or enumeration procedure) and/or diluted prior to the identifying or enumerating procedure.

In yet another aspect, the present disclosure provides a kit for the enrichment, detection, or both, of anaerobic microorganisms or microaerophilic microorganisms. The kit includes a sealable container; an oxygen scavenging system comprising effective amounts of i) an enzyme of an oxidoreductase family and ii) a substrate for said enzyme; said oxygen scavenging system being activated upon hydration with a predetermined volume of aqueous medium thereby creating an environment substantially depleted or devoid of oxygen. The kit may further include additional components, if desired, selected to permit use of the kit for one or more particular applications. In any embodiment of the kit, the container is substantially impermeable to oxygen.

In any embodiment of a kit of the present disclosure, the container may be selected from a pouch, and envelope, a sealed wrapping, a bag, a can, a jar, a barrel, a box or barrier bag, a zippered bag (e.g., a ZIPLOC storage bag), a dense lab bag (e.g., STOMACHER blender bag), a flask with stopper, a bottle with stopper, or any form of sealed containment suitable for holding cultures of anaerobic or microaerophilic microorganisms. In any embodiment, the container may be sealed using a stopper, a septum (e.g., a pierceable, self-sealing septum), a screwcap, and/or a heat seal.

The container may be formed of suitable polymeric materials which include polyvinyl chloride, polyethylene, polycarbonate, polystyrene, polyvinyledene chloride, polyacrylonitriles, polyethylene vinyl acetate copolymer, polymethacrylonitrile, cellulose acetate, cellulose acetate butyrate, cellulose diacetate, Neoprene®, Teflon®, polysiloxane or mixtures and/or laminates thereof. In any embodiment, the container may be made of glass.

As per the invention the kit may comprise the enzyme-substrate system deployed in a variety of formats such as a tablet form (e.g., pills, donuts, or small spheres), a lyophilized form, a spray coating inside the bag, a sachet, or a powdered quick dissolve media.

In any embodiment, the kit may also comprise additional components such as at least one indicator selected from a pH indicator, an indicator for indicating the presence or absence of oxygen, instruction for use, or a combination of any two or more of the foregoing additional components.

EXEMPLARY EMBODIMENTS

Embodiment A is a method, comprising:
forming an aqueous mixture in a container; the mixture comprising a sample containing an anaerobic microorganism or a microaerophilic microorganism, a predefined volume of a medium that supports growth of an anaerobic microorganism or a microaerophilic microorganism, and an oxygen scavenging system;
wherein said oxygen scavenging system comprises effective amounts of i) an enzyme of an oxidoreductase family and ii) a substrate for said enzyme;
wherein said oxygen scavenging system is activated upon hydration thereby depleting dissolved oxygen in the medium to a concentration that facilitates growth of the anaerobic microorganism or microaerophilic microorganism; and
incubating the aqueous mixture under conditions to facilitate at least one cell division of said anaerobic microorganism or microaerophilic microorganism.
Embodiment B is a method, comprising:
forming an aqueous mixture in a container; the mixture comprising a sample containing an anaerobic microorganism or a microaerophilic microorganism, a predefined volume of a medium that supports growth of an anaerobic microorganism or a microaerophilic microorganism, and an oxygen scavenging system;
wherein said oxygen scavenging system comprises effective amounts of i) an enzyme of an oxidoreductase family and ii) a substrate for said enzyme;
wherein said oxygen scavenging system is activated upon hydration thereby depleting dissolved oxygen in the medium to a concentration that facilitates growth of the anaerobic microorganism or microaerophilic microorganism;

wherein the enzyme is selected from a group consisting of ascorbic acid oxidase and laccase; and incubating the aqueous mixture under conditions to facilitate at least one cell division of said anaerobic microorganism or microaerophilic microorganism.

Embodiment C is the method of Embodiment A or Embodiment B, wherein depleting dissolved oxygen in the medium to a concentration that facilitates growth of the anaerobic microorganism or microaerophilic microorganism comprises depleting dissolved oxygen in the medium to a concentration of about 100 µM or less.

Embodiment D is the method of Embodiment A or Embodiment B, wherein depleting dissolved oxygen in the medium to a concentration that facilitates growth of the anaerobic microorganism or microaerophilic microorganism comprises depleting dissolved oxygen in the medium to a concentration of about 10 µM or less.

Embodiment E is the method of Embodiment A or Embodiment B, wherein depleting dissolved oxygen in the medium to a concentration that facilitates growth of the anaerobic microorganism or microaerophilic microorganism comprises depleting dissolved oxygen in the medium to a concentration of about 1 µM or less.

Embodiment F is the method of any one of the preceding Embodiments, further comprising:

detecting growth of the anaerobic microorganism or the microaerophilic microorganism.

Embodiment G is the method of Embodiment F, further comprising:

analyzing the anaerobic microorganism or microaerophilic microorganism to associate the anaerobic microorganism or microaerophilic microorganism with a genus, a species, or a group of microorganisms characterized by a feature other than its ability to grow in an oxygen-containing environment.

Embodiment H is the method of any one of the preceding Embodiments, wherein forming an aqueous mixture in a container comprises forming an aqueous mixture in a container that is substantially impermeable to oxygen.

Embodiment I is the method of any one of the preceding Embodiments, wherein the enzyme comprises ascorbate oxidase, wherein the substrate is selected from the group comprising ascorbic acid or a salt thereof, a derivative of ascorbic acid or a salt thereof, hydroquinone, pyrogallol, catechol, or a mixture of any two or more of the foregoing substrates.

Embodiment J is the method of Embodiment I, wherein the derivative of ascorbic acid is selected from the group consisting of D-iso-ascorbate, D-araboascorbic acid, 6-amino-L-ascorbate, 6-deoxy-1-ascorbate, D-erythroascorbate, 6-O-phenyl-L-ascorbate, and 6-S-phenyl-L-ascorbate.

Embodiment K is the method of any one of Embodiments A through H, wherein the enzyme comprises laccase, wherein the substrate is selected from the group consisting of a phenol, L-tyrosine, o-diphenol and p-diphenol, 2,6-dimethoxyphenol, and mixtures of any two or more of the foregoing substrates.

Embodiment L is the method of any one of the preceding Embodiments, wherein said method promotes enrichment of anaerobic or microaerophilic microorganisms in a mixed microbial population comprising an aerobic microorganism and at least one of a microaerophilic microorganism or an anaerobic microorganism.

Embodiment M is the method of any one of the preceding Embodiments wherein, after forming the aqueous mixture, the enzyme is present in the mixture at a concentration of at least 1000 units/L.

Embodiment N is the method of Embodiment M wherein, after forming the aqueous mixture, the enzyme is present in the mixture at a concentration of at least 2000 units/L.

Embodiment O is the method of Embodiment M wherein, after forming the aqueous mixture, the enzyme is present in the mixture at a concentration of at least 4000 units/L.

Embodiment P is the method of any one of the preceding Embodiments wherein, after forming the aqueous mixture, the substrate is present in the mixture at a concentration of about 0.1 to 100 mg/ml.

Embodiment Q is the method of Embodiment P wherein, after forming the aqueous mixture, the substrate is present in the mixture at a concentration of about 0.1 to 50 mg/ml.

Embodiment R is the method of Embodiment P wherein, after forming the aqueous mixture, the substrate is present in the mixture at a concentration of about 0.1 to 10 mg/ml.

Embodiment S is the method of Embodiment P wherein, after forming the aqueous mixture, the substrate is present in the mixture at a concentration of about 0.1 to 5 mg/ml.

Embodiment T is the method of any one of the preceding Embodiments wherein; prior to forming the aqueous mixture; at least a portion of the oxygen-scavenging system is deployed as a solution, a tablet, a sachet, a coating disposed on an inside surface of a wall of the container, or a powder.

Embodiment U is the method of any one of the preceding Embodiments, forming the aqueous mixture comprises contacting a mixture of the oxygen scavenging system and the sample with the medium.

Embodiment V is the method of any one of the preceding Embodiments, wherein forming the aqueous mixture comprises contacting the oxygen scavenging system with an aqueous liquid mixture comprising the sample and the medium.

Embodiment W is the method of any one of the preceding Embodiments, wherein the sample comprises material collected from a source selected from the group consisting of air, water, a food, a beverage, an animal, a biological tissue, a biological fluid, and an environmental surface.

Embodiment X is the method of any one of the preceding Embodiments, wherein the anaerobic microorganism is an obligate anaerobe or a facultative anaerobe.

Embodiment Y is the method of any one of the preceding Embodiments, wherein the microorganism belongs to a genus selected from the group consisting of *Bacteroides, Fusobacterium, Porphyromonas, Prevotella, Actinomyces, Bifidobacterium, Clostridium, Peptostreptococcus, Propionibacterium, Lactobacillus, Peptococcus, Peptostreptococcus, Veillonella, Staphylococcus, Streptococcus, Escherichia, Listeria* and *Shewanella*.

Embodiment Z is the method of any one of the preceding Embodiments, wherein the microaerophilic microorganism belongs to a genus selected from the group consisting of *Campylobater, Helicobacter* and *Borrelia*.

Embodiment AA is the method of Embodiment Z, wherein the microaerophilic microorganism of the *Campylobater* genus belongs to a species selected from the group consisting of *Campylobater jejuni* or *Campylobater coli*.

Embodiment AB is the method of any one of the preceding Embodiments, wherein the container is made of a polymeric material.

Embodiment AC is the method of Embodiment AB, wherein the polymeric material is selected from the group consisting of polyvinyl chloride, polyethylene, polycarbonate, polystyrene, polyvinyledene chloride, polyvinylidene copolymer, polyacrylonitriles, polymethacrylonitrile, cellulose acetate, cellulose acetate butyrate, cellulose diacetate, Neoprene®, Teflon®, polysiloxane and mixtures and laminates thereof.

Embodiment AD is the method of any one of Embodiments F through AC, wherein detecting growth of the microorganism comprises measuring or detecting an observable change of the medium after incubation.

Embodiment AE is the method of Embodiment AD, wherein measuring or detecting an observable change of the medium comprises measuring or observing turbidity.

Embodiment AF is the method of Embodiment AD, wherein the growth of the anaerobic or microaerophilic microorganism is detected using an indicator agent.

Embodiment AG is the method of any one of the preceding Embodiments, further comprising:
placing a material that indicates the presence or absence of oxygen into the container.

Embodiment AH is the method of Embodiment AG, wherein placing a material into the container comprises placing the material into fluid communication with the medium.

Embodiment AI is the method of Embodiment AG or Embodiment AH, wherein the material indicates the presence or absence of oxygen in the container by means of a color change.

Embodiment AJ is the method of any one of Embodiments AG through AI, wherein said material is methylene blue.

Embodiment AK is the method of any one of the preceding Embodiments, wherein depleting dissolved oxygen in the medium to a concentration that facilitates growth comprises depleting the dissolved oxygen to the concentration in about 60 minutes or less.

Embodiment AL is the method of any one of the preceding Embodiments, wherein depleting dissolved oxygen in the medium to a concentration that facilitates growth comprises depleting the dissolved oxygen to the concentration in about 30 minutes or less.

Embodiment AM is a culture system for culturing a microaerophilic microorganism or an anaerobic microorganism, said system comprising:
effective amounts of i) an enzyme of an oxidoreductase family and ii) a substrate for said enzyme;
a container; and
a predetermined volume of aqueous medium that supports growth of said anaerobic or microaerophilic microorganism;
wherein the effective amounts are effective to deplete dissolved oxygen in the predetermined volume to a concentration that facilitates growth of a microaerophilic microorganism or an obligately-anaerobic microorganism.

Embodiment AN is a culture system for culturing a microaerophilic microorganism or an anaerobic microorganism, said system comprising:
effective amounts of i) an enzyme of an oxidoreductase family and ii) a substrate for said enzyme, wherein the enzyme is selected from a group consisting of ascorbic acid oxidase and laccase;
a container; and
a predetermined volume of aqueous medium that supports growth of said anaerobic or microaerophilic microorganism;
wherein the effective amounts are effective to deplete dissolved oxygen in the predetermined volume to a concentration that facilitates growth of a microaerophilic microorganism or an obligately-anaerobic microorganism.

Embodiment AO is the culture system of Embodiment AM or Embodiment AN, wherein the container is substantially impermeable to oxygen.

Embodiment AP is the culture system of any one of Embodiments AM through AO, wherein the container is sealable.

Embodiment AQ is the culture system of Embodiment AP, wherein the container is resealable.

Embodiment AR is the culture system of any one of Embodiments AM through AQ, wherein the effective amounts are effective to deplete the dissolved oxygen in the predefined volume to about 100 µM or less.

Embodiment AS is the culture system of any one of Embodiments AM through AQ, wherein the effective amounts are effective to deplete the dissolved oxygen in the predefined volume to about 10 µM or less.

Embodiment AT is the culture system of any one of Embodiments AM through AQ, wherein the effective amounts are effective to deplete the dissolved oxygen in the predefined volume to about 1 µM or less.

Embodiment AU is the culture system of any one of Embodiments AM through AT, wherein the effective amounts are effective to deplete the dissolved oxygen in the predefined volume to the concentration that facilitates the growth in about 60 minutes or less.

Embodiment AV is the culture system of any one of Embodiments AM through Embodiment AT, wherein the effective amounts are effective to deplete the dissolved oxygen in the predefined volume to the concentration that facilitates the growth in about 30 minutes or less.

Embodiment AW is a kit, comprising:
sealable container; and
an oxygen scavenging system comprising i) an enzyme of an oxidoreductase family and ii) a substrate for said enzyme.

Embodiment AX is a kit, comprising:
a sealable container; and
an oxygen scavenging system comprising i) an enzyme of an oxidoreductase family and ii) a substrate for said enzyme, wherein the enzyme is selected from a group consisting of ascorbic acid oxidase and laccase.

Embodiment AY is the kit of Embodiment AW or Embodiment AX, wherein the container is substantially impermeable to oxygen.

Embodiment AZ is the kit of any one of Embodiments AW through AY, wherein the sealable container is resealable.

Embodiment BA is the kit of any one of Embodiments AW through AZ, wherein the enzyme is allocated in one or more first vessel, each first vessel having an amount of enzyme effective react with the enzyme substrate to deplete dissolved oxygen in a predetermined volume of aqueous medium to a dissolved oxygen concentration that facilitates growth of an anaerobic microorganism or a microaerophilic microorganism.

Embodiment BB is the kit of any one of Embodiments AW through BA, wherein the substrate is allocated in the one or more first vessel or one or more second vessel, each first vessel or second vessel having an amount of substrate effective to react with the enzyme to deplete dissolved oxygen in a predetermined volume of aqueous medium to a dissolved oxygen concentration that facilitates growth of an anaerobic microorganism or a microaerophilic microorganism.

Embodiment BC is the kit of Embodiment BA or Embodiment BB, wherein the first vessel and/or the second vessel is the container.

Embodiment BD is the kit of any one of Embodiments AW through BC, wherein the container is selected from the group consisting of a pouch, an envelope, a sealed wrapping, a bag, a can, a jar, a barrel, a flask, and a bottle.

Embodiment BE is the kit of any one of Embodiments AW through BD, wherein the container is made of a polymeric material selected from polyvinyl chloride, polyethylene, polycarbonate, polystyrene, polyvinyledene chloride, polyacrylonitriles, polymethacrylonitrile, cellulose acetate, cellulose acetate butyrate, cellulose diacetate, Neoprene®, Teflon®, polysiloxane and mixtures thereof.

Embodiment BF is the kit of any one of Embodiments AW through BD, wherein the container is made of glass.

Embodiment BG is the kit of any one of Embodiments AW through BF, wherein the enzyme and/or the substrate is disposed in the kit in a form selected from a group consisting of a tablet, a sachet, a coating disposed on an inside surface of a wall of the container, or a powder.

Embodiment BH is the kit of any one of Embodiments AW through BG, wherein the kit further comprises a material that can be placed into the container to indicate a presence or absence of oxygen in the container.

Embodiment BI is the kit of Embodiment BH, wherein the material indicates the presence or absence of oxygen in the container by means of a color change.

Embodiment BJ is the kit of Embodiment BH or Embodiment BI, wherein the material comprises methylene blue.

Embodiment BK is the kit of any one of Embodiments AW through BJ, wherein the kit further comprises a pH indicator.

Embodiment BL is the kit of any one of Embodiments AW through BK, wherein the kit further comprises instruction for use.

The following examples are provided to better illustrate the claimed invention and are not to be interpreted in any way as limiting the scope of the invention. All specific materials, and methods described below, in whole or in part, fall within the scope of the invention. These specific compositions, materials, and methods are not intended to limit the invention, but merely to illustrate specific embodiments falling within the scope of the invention. One skilled in the art may develop equivalent materials, and methods without the exercise of inventive capacity and without departing from the scope of the invention. It will be understood that many variations can be made in the procedures herein described while still remaining within the bounds of the invention. It is the intention of the inventors that such variations are included within the scope of the invention.

EXAMPLES

Example 1-To Demonstrate the Enrichment and Detection of Microaerophilic and Anaerobic Microorganisms Organisms: *Campylobacter jejuni/Campylobacter coli* and *Clostridium sporogenes*

Culture medium used: Bolton's broth (enrichment medium)

TABLE 1

Composition of Bolton's broth.

| Concentration | Component | Source of Component |
|---|---|---|
| 10 g/L | Peptone from meat | Becton Dickinson; Franklin Lakes, NJ |
| 5 g/L | Lactalbumin | Part No. L3065; Spectrum Chemicals; New Brunswick, NJ |

TABLE 1-continued

Composition of Bolton's broth.

| Concentration | Component | Source of Component |
|---|---|---|
| 5 g/L | Yeast extract | CAS# 8013-01-2; EMD Millipore; Billerica, MA |
| 5 g/L | Sodium chloride | CAS# 7647-14-5; US Biochemical Corporation; Cleveland, OH |
| 1.0 g/L | alpha-Ketoglutaric acid | CAS# 328-50-7; Sigma-Aldrich; St. Louis, MO |
| 0.5 g/L | sodium pyruvate | CAS# 113-24-6; Sigma-Aldrich |
| 0.6 g/L | sodium carbonate | CAS Number 497-19-8; Sigma-Aldrich; |
| 0.01 g/L | Hemin | Sigma-Aldrich |
| 0.15 g/L | Ferrous sulfate heptahydrate | CAS# 7782-63-0; Sigma-Aldrich |

The components of the broth were dissolved in deionized water and the mixture was autoclaved. After sterilization, approximately 225 mL of the broth was distributed into barrier bags (Associated Bag Company, Milwaukee, Wis.; part number 185-100) that hold a liquid volume of 500 mL.

Stock solutions of ascorbic acid oxidase (Part #061A0500; Calzyme Laboratories; San Luis Obispo, Calif.) and sodium ascorbate (CAS#134-03-2; Sigma-Aldrich) were prepared in deionized water.

Enrichment and Detection of Microaerophilic Organisms: *Campylobacter jejuni/Campylobacter Coli*:

The sample (a diluted overnight culture of *Campylobacter jejuni/Campylobacter coli* in Butterfields buffer) was added to the each bag of medium to attain a final concentration of about 50 CFU (about 0.002 CFU/10 μL) in the culture medium. The bags were sealed using the zipper-type seal at the opening of each bag. Subsequently, the culture medium in the bag was supplemented with appropriate volumes of the stock solutions to attain a final concentration of 4K units/L of enzyme ascorbate oxidase and 1.31 mg/mL of the substrate sodium ascorbate in the culture medium. Each sealed bag had approximately 30-100 mL of ambient air sealed in the bag with the medium. The sealed bags were incubated in ambient atmosphere at 42° C. for 48 hours. Another bag was prepared and incubated as above but was not spiked with the sample microorganisms and served as a sterility control for the reagents and bags. The uninoculated control was not visibly turbid, indicating no growth due to contamination from the components or the bags. The bags inoculated with *Campylobacter* were non-turbid as well, indicating the microorganisms did not grow to a cell concentration of greater than about $10^7$/mL. A loopful (ca. 10 microliters) from each of the *Campylobacter* enrichment cultures and the control medium was then streaked out on to non-selective charcoal agar and the plates were incubated overnight. Growth (i.e., >100 colonies/plate) was observed on the plates inoculated with *Campylobacter* enrichment culture samples confirming that the microaerophilic bacteria grew in the oxygen-depleted environment created in the enrichment cultures. No growth was observed on the plates inoculated from the control medium.

Enrichment and Detection of Obligately-Anaerobic Bacteria: e.g., *Clostridium sporogenes*.

The sample (a diluted overnight culture of *Clostridium sporogenes* in Butterfields buffer) was added to a bag of medium to attain a final concentration of about 50 CFU/mL in the culture medium. Subsequently, the culture medium in the bag was supplemented with appropriate volumes of the stock solutions to attain a final concentration of 4K units/L of enzyme ascorbate oxidase and 6.55 mg/mL of the substrate sodium ascorbate in the culture medium. A control bag (without bacteria) was prepared as described above. The bags were sealed using the pressure seal at the opening of each bag. Each sealed bag had approximately 30-100 mL of ambient air sealed in the bag with the medium. The sealed bags were incubated in ambient atmosphere at 37° C. for 48 hours. Growth was indicated by visible turbidity in the bags inoculated with *Clostridium sporogenes*. The uninoculated control was not visibly turbid, indicating no growth due to contamination from the components or the bags.

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

The invention claimed is:

1. A method, comprising:
forming an aqueous mixture in a container; the mixture comprising a sample containing a microaerophilic microorganism of a genus selected from the group consisting of *Campylobacter, Borrelia* and *Helicobacter*, a predefined volume of a medium that supports growth of a microaerophilicmicroorganism, and an oxygen scavenging system;
wherein said oxygen scavenging system comprises effective amounts of i) an enzyme of an oxidoreductase family and ii) a substrate for said enzyme;
activating said oxygen scavenging system by hydration thereby depleting dissolved oxygen in the medium to a concentration of 10 µM or less;
wherein the enzyme is selected from a group consisting of ascorbic acid oxidase and laccase; and
incubating the aqueous mixture to facilitate at least one cell division of said microaerophilic microorganism of a genus selected from the group consisting of *Campylobacter, Borrelia* and *Helicobacter*.

2. The method of claim 1, further comprising: detecting growth of the microaerophilic microorganism of a genus selected from the group consisting of *Campylobacter, Borrelia* and *Helicobacter*.

3. The method of claim 2, further comprising: analyzing the microaerophilic microorganism of a genus selected from the group consisting of *Campylobacter, Borrelia* and *Helicobacter* to associate the microaerophilic microorganism with a genus, a species, or a group of microorganisms characterized by a feature other than its ability to grow in an oxygen-containing environment.

4. The method of claim 1, wherein the enzyme comprises ascorbate oxidase, wherein the substrate is selected from the group comprising ascorbic acid or a salt thereof, a derivative of ascorbic acid or a salt thereof, hydroquinone, pyrogallol, catechol, or a mixture of any two or more of the foregoing substrates.

5. The method of claim 1, wherein the enzyme comprises laccase, wherein the substrate is selected from the group consisting of a phenol, L-tyrosine, o-diphenol and p-diphenol, 2,6-dimethoxyphenol, and mixtures of any two or more of the foregoing substrates.

6. The method of claim 1, wherein said method promotes the enrichment of anaerobic or microaerophilic microorganisms in a mixed microbial population comprising an aerobic microorganism and at least one of a microaerophilic microorganism or an anaerobic microorganism.

7. The method of claim 1 wherein, after forming the aqueous mixture, the enzyme is present in the mixture at a concentration of at least 1000 units/L.

8. The method of claim 1, after forming the aqueous mixture, the substrate is present in the mixture at a concentration of about 0.1 to 100 mg/ml.

9. The method of claim 1 wherein; prior to forming the aqueous mixture; at least a portion of the oxygen-scavenging system is deployed as a solution, a tablet, a sachet, a coating disposed on an inside surface of a wall of the container, or a powder.

10. The method of claim 1, forming the aqueous mixture comprises contacting a mixture of the oxygen scavenging system and the sample with the medium.

11. The method of claim 1, wherein forming the aqueous mixture comprises contacting the oxygen scavenging system with an aqueous liquid mixture comprising the sample and the medium.

12. The method of claim 1, wherein depleting dissolved oxygen in the medium to a concentration that facilitates the growth comprises depleting the dissolved oxygen to the concentration in about 60 minutes or less.

13. A method, comprising:
forming an aqueous mixture in a container; the mixture comprising a sample containing a microaerophilic microorganism of a genus selected from the group consisting of *Campylobacter, Borrelia* and *Helicobacter* and aerobic microorganisms in a concentration that it at least 1,000 times higher than the concentration of the microaerophilic microorganism, a predefined volume of a medium that is capable of supporting the growth of the microaerophilic microorganism, and an oxygen scavenging system;
wherein said oxygen scavenging system comprises effective amounts of i) an enzyme of an oxidoreductase family and ii) a substrate for said enzyme;
activating said oxygen scavenging system by hydration thereby depleting dissolved oxygen in the medium to a concentration;
wherein the enzyme is selected from a group consisting of ascorbic acid oxidase and laccase; and
incubating the aqueous mixture under conditions suitable to facilitate at least one cell division of the microaerophilic microorganism;
wherein depleting dissolved oxygen in the medium to a concentration that facilitates the growth comprises depleting the dissolved oxygen to the concentration in about 60 minutes or less; and
wherein the concentration that facilitates the growth is 10 µM or less.

14. The method of claim 13, wherein the enzyme comprises ascorbate oxidase, wherein the substrate is selected from the group comprising ascorbic acid or a salt thereof, a derivative of ascorbic acid or a salt thereof, hydroquinone, pyrogallol, catechol, or a mixture of any two or more of the foregoing substrates.

15. The method of claim 13, wherein the enzyme comprises laccase, wherein the substrate is selected from the group consisting of a phenol, L-tyrosine, o-diphenol and p-diphenol, 2,6-dimethoxyphenol, and mixtures of any two or more of the foregoing substrates.

16. The method of claim 13 wherein, after forming the aqueous mixture, the enzyme is present in the mixture at a concentration of at least 1000 units/L.

17. The method of claim 13, after forming the aqueous mixture, the substrate is present in the mixture at a concentration of about 0.1 to 100 mg/ml.

* * * * *